US00PP30691P2

(12) United States Plant Patent
Ruigrok

(10) Patent No.: US PP30,691 P2
(45) Date of Patent: Jul. 9, 2019

(54) ***DAHLIA* PLANT NAMED 'BKDAMAGRB'**

(50) Latin Name: *Dahlia hybrida*
Varietal Denomination: BKDAMAGRB

(71) Applicant: Sanne Helena Ruigrok, Hillegom (NL)

(72) Inventor: Sanne Helena Ruigrok, Hillegom (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 15/932,678

(22) Filed: Apr. 6, 2018

(51) Int. Cl.
*A01H 5/02* (2018.01)

(52) U.S. Cl.
USPC ..... Plt./321

(58) Field of Classification Search
USPC ..... Plt./321
See application file for complete search history.

*Primary Examiner* — Annette H Para
(74) *Attorney, Agent, or Firm* — C. A. Whealy

(57) ABSTRACT

A new and distinct cultivar of *Dahlia* plant named 'BKDAMAGRB', characterized by its broadly upright plant habit; moderate basal branching habit; dense and bushy growth habit; large dark green-colored leaves; and large decorative type inflorescences with white and red purple bi-colored ray florets.

2 Drawing Sheets

Botanical designation: *Dahlia hybrida.*
Cultivar denomination: 'BKDAMAGRB'.

BACKGROUND OF THE INVENTION

The present invention relates to a new and distinct cultivar of *Dahlia* plant, botanically known as *Dahlia hybrida* and hereinafter referred to by the name 'BKDAMAGRB'.

The new *Dahlia* plant is a product of a planned breeding program conducted by the Inventor in Hillegom, The Netherlands. The objective of the breeding program is to create new large container *Dahlia* plants with large and attractive decorative type inflorescences.

The new *Dahlia* plant originated from a cross-pollination in September, 2013 in Hillegom, The Netherlands of a proprietary selection of *Dahlia hybrida* identified as code number FET.S12.011.003, not patented, as the female, or seed, parent with a proprietary selection of *Dahlia hybrida* identified as code number FET.S12.003.021, not patented, as the male, or pollen, parent. The new *Dahlia* plant was discovered and selected by the Inventor as a single flowering plant from within the progeny of the stated cross-pollination in a controlled greenhouse environment in Hillegom, The Netherlands in October, 2015.

Asexual reproduction of the new *Dahlia* plant by vegetative terminal cuttings in a controlled greenhouse environment in Maasdijk, The Netherlands since February, 2016 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAMAGRB'. These characteristics in combination distinguish 'BKDAMAGRB' as a new and distinct *Dahlia* plant:

1. Broadly upright plant habit.
2. Moderate basal branching habit; dense and bushy growth habit.
3. Large dark green-colored leaves.
4. Large decorative type inflorescences with white and red purple bi-colored ray florets.

Plants of the new *Dahlia* differ primarily from plants of the female parent selection in the following characteristics:

1. Plants of the new *Dahlia* have decorative type inflorescences whereas plants of the female parent selection have cactus type inflorescences.
2. Ray floret colors of plants of the new *Dahlia* are brighter and more vivid than ray floret colors of plants of the female parent selection.

Plants of the new *Dahlia* differ primarily from plants of the male parent selection in the following characteristics:

1. Plants of the new *Dahlia* have decorative type inflorescences whereas plants of the male parent selection have semi-cactus type inflorescences.
2. Ray florets of plants of the new *Dahlia* are white and red purple in color whereas ray floret of plants of the male parent selection are pink in color.

Plants of the new *Dahlia* can be compared to plants of *Dahlia hybrida* 'XXL Veracruz', not patented. In side-by-side comparisons, plants of the new *Dahlia* differ from plants of 'XXL Veracruz' in the following characteristics:

1. Plants of the new *Dahlia* are more upright and taller than plants of 'XXL Veracruz'.
2. Plants of the new *Dahlia* and 'XXL Veracruz' differ in ray floret color as plants of 'XXL Veracruz' have light pink and violet bi-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'BKDAMAGRB' grown in a container.

The photograph on the second sheet is a close-up view of a typical inflorescence of 'BKDAMAGRB'.

DETAILED BOTANICAL DESCRIPTION

The aforementioned photographs and the following observations and measurements describe plants grown during the winter in 19-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were nine weeks old when the photographs and description were taken. To induce inflorescence initiation and development, plants were grown under short nyctoperiod (long day) conditions. In the following description, color references are made to The Royal Horticultural Society Colour Chart, 2015 Edition, except where general terms of ordinary dictionary significance are used.

Botanical classification: *Dahlia hybrida* 'BKDAMAGRB'.

Parentage:

- *Female, or seed, parent*.—Proprietary selection of *Dahlia hybrida* identified as code number FET.S12.011.003, not patented.
- *Male, or pollen, parent*.—Proprietary selection of *Dahlia hybrida* identified as code number FET.S12.003.021, not patented.

Propagation:

- *Type*.—By vegetative terminal cuttings.
- *Time to initiate roots, summer*.—About 16 days at temperatures ranging from 18° C. to 21° C.
- *Time to initiate roots, winter*.—About 19 days at temperatures ranging from 19° C. to 21° C.
- *Time to produce a rooted young plant, summer*.—About 23 days at temperatures ranging from 18° C. to 21° C.
- *Time to produce a rooted young plant, winter*.—About 25 days at temperatures ranging from 19° C. to 21° C.
- *Root description*.—Medium in thickness, fibrous; typically white in color, actual color of the roots is dependent on substrate composition, water quality, fertilizers, substrate temperature and physiological age of roots; tuber development has not been observed on plants of the new *Dahlia*.
- *Rooting habit*.—Moderately freely branching; medium density.

Plant description:

- *Plant and growth habit*.—Broadly upright and mounding plant form; overall plant shape, flattened globular; moderate basal branching habit with about four primary branches developing per plant; inflorescences held above and beyond the foliar plane on strong peduncles; bushy and dense growth habit; pinching is not required but will improve branching habit; moderately vigorous growth habit.
- *Plant height, soil level to top of foliar plane*.—About 20.8 cm.
- *Plant height, soil level to top of floral plane*.—About 36.6 cm.
- *Plant diameter or spread*.—About 37.2 cm.
- *Lateral branches*.—Length: About 12.7 cm. Diameter: About 8 mm. Internode length: About 2.2 cm. Aspect: Primary branches are about 20° from vertical; secondary branches, about 30° from primary branch axis. Strength: Moderately strong to strong. Texture and luster: Smooth, glabrous; glossy. Color, developing: Close to 143A. Color, developed: Close to 143C strongly tinged with close to N186C and N200A.

Leaf & leaflet description:

- *Arrangement*.—Leaves opposite and compound with three or five leaflets.
- *Length, compound leaves*.—About 18.5 cm.
- *Length, terminal leaflets*.—About 13.8 cm.
- *Length, lateral leaflets*.—About 9.8 cm.
- *Width, compound leaves*.—About 20.1 cm.
- *Width, terminal leaflets*.—About 5.5 cm.
- *Width, lateral leaflets*.—About 4.3 cm.
- *Shape, compound leaves in overall outline*.—Broadly ovate.
- *Shape, leaflets*.—Ovate to elliptic.
- *Apex, leaflets*.—Apiculate.
- *Base, leaflets*.—Attenuate.
- *Margin, leaflets*.—Coarsely serrate.
- *Venation pattern, leaflets*.—Pinnate.
- *Texture and luster, upper surface, leaflets*.—Slightly rugose, glabrous; slightly velvety; slightly glossy.
- *Texture and luster, lower surface, leaflets*.—Slightly rugose, sparsely pubescent along venation; matte.
- *Color*.—Developing leaflets, upper surface: Close to NN137A. Developing leaflets, lower surface: Close to 147B. Fully expanded leaflets, upper surface: Close to between 139A and 147A; venation, close to 143A. Fully expanded leaflets, lower surface: Close to 191A; venation, close to 146B.
- *Petioles, leaflets*.—Length: About 2.8 cm. Diameter: About 5 mm. Strength: Moderately strong. Texture and luster, upper surface: Smooth, glabrous; glossy. Texture and luster, lower surface: Smooth, glabrous; slightly glossy. Color, upper surface: Close to 146C tinged with close to N200A. Color, lower surface: Close to 146C.

Inflorescence description:

- *Appearance and arrangement*.—Large decorative type inflorescences with ray and disc florets forming acropetally on a receptacle; inflorescences positioned above and beyond the foliar plane on strong peduncles; inflorescences face mostly upright to slightly outwardly; freely flowering habit with about 18 inflorescences develop per plant.
- *Fragrance*.—None detected.
- *Flowering response and flowering period*.—Plants begin flowering about 69 days after planting; plants flower continuously during the autumn into the winter in The Netherlands.
- *Post-production longevity*.—Inflorescences maintain good substance for about ten days on the plant; inflorescences persistent.
- *Inflorescence buds*.—Height: About 1.7 cm. Diameter: About 1.6 cm. Shape: Roughly globular. Texture and luster: Smooth, glabrous; glossy. Color: Close to N144B; towards the base, close to 144A and towards the apex, close to 75A.

*Inflorescence size*.—Diameter: About 12.1 cm. Depth (height): About 8.5 cm. Disc diameter: About 1.9 cm, typically inconspicuous.

*Receptacles*.—Height: About 1.3 cm. Diameter: About 1.1 cm. Shape: Bluntly sagittate. Color: Close to 147D.

*Ray florets*.—Quantity per inflorescence and arrangement: About 160 arranged in about eight whorls. Length: About 5.5 cm. Width: About 2 cm. Shape: Oblanceolate. Apex: Retuse. Base: Broadly attenuate. Margin: Entire; distally, strongly revolute. Aspect: Varying from −20° to 50° from horizontal. Texture and luster, upper surface: Smooth, glabrous; velvety; matte. Texture and luster, lower surface: Smooth, glabrous; moderately velvety; slightly glossy. Color: When opening, upper surface: Proximally, close to NN155A; distally, close to between 61B and 67A; fading towards the apex to close to N74A. When opening, lower surface: Proximally, close to 150D; distally, close to 64B to 64C. Fully opened, upper surface: Close to NN155C; at the margins and towards the apex, close to N66B to N66C; venation, similar to lamina colors; with development, color becoming closer to 155C and at the margins and towards the apex, closer to 61B and 64A. Fully opened, lower surface: Close to NN155B; at the margins and towards the apex, close to 68B; venation, close to NN155B and 68B; with development, color becoming closer to 155B to 155C and at the margins and towards the apex, closer to 70B.

*Disc florets*.—Quantity per inflorescence and arrangement: About 40 massed at the center of the inflorescence in about five spiral whorls; typically inconspicuous. Length: About 1.2 cm. Diameter: About 7 mm. Shape: Tubular, elongated; apices, acute. Texture and luster, inner and outer surfaces: Smooth, glabrous; glossy. Color, when opening, inner and outer surfaces: Close to 12A; towards the base, close to 150C. Color, fully opened, inner and outer surfaces: Close to 14B; mid-section, close to 1B; towards the base, close to 150C.

*Phyllaries*.—Quantity per inflorescence and arrangement: About six arranged in a single whorl. Length: About 1.8 cm. Width: About 7 mm. Shape: Narrowly obovate. Apex: Acute. Base: Cuneate. Margin: Entire. Texture and luster, upper and lower surfaces: Smooth, glabrous; glossy. Color, upper and lower surfaces: Close to NN137B.

*Ray floret bracts*.—Quantity per inflorescence and arrangement: One subtending each ray floret. Length: About 2.3 cm. Width: About 7 mm. Shape: Narrowly ovate. Apex: Acute. Base: Broadly cuneate. Margin: Entire. Texture and luster, upper and lower surfaces: Smooth, glabrous; glossy. Color, upper and lower surfaces: Close to 150C to 150D; towards the base, close to 145B.

*Peduncles*.—Length, terminal peduncle: About 15.5 cm. Diameter, terminal peduncle: About 4 mm. Strength: Strong. Texture and luster: Smooth, glabrous; moderately glossy. Color: Close to between 146A and 148A.

*Reproductive organs*.—Androecium, present on disc florets only: Quantity per floret: About five. Filament length: About 4 mm. Filament color: Close to 150D. Anther shape: Narrowly oblong. Anther length: About 8 mm. Anther color: Close to 13A to 13B. Pollen amount: Moderate. Pollen color: Close to 17A. Gynoecium, present on disc florets only: Quantity per floret: One. Pistil length: About 1.2 cm. Style length: About 8 mm. Style color: Close to 154C. Stigma diameter: About 6 mm. Stigma shape: Cleft. Stigma color: Close to 14A. Ovary color: Close to 145D. Seeds and fruits: Seed and fruit development have not been observed on plants of the new *Dahlia* to date.

Disease & pest resistance: To date, plants of the new *Dahlia* have not been observed to be resistant to pathogens and pests common to *Dahlia* plants.

Temperature tolerance: Plants of the new *Dahlia* have been observed to tolerate high temperatures of about 35° C. and to be suitable for USDA Hardiness Zones 9 to 11.

It is claimed:

1. A new and distinct *Dahlia* plant named 'BKDAM-AGRB' as illustrated and described.

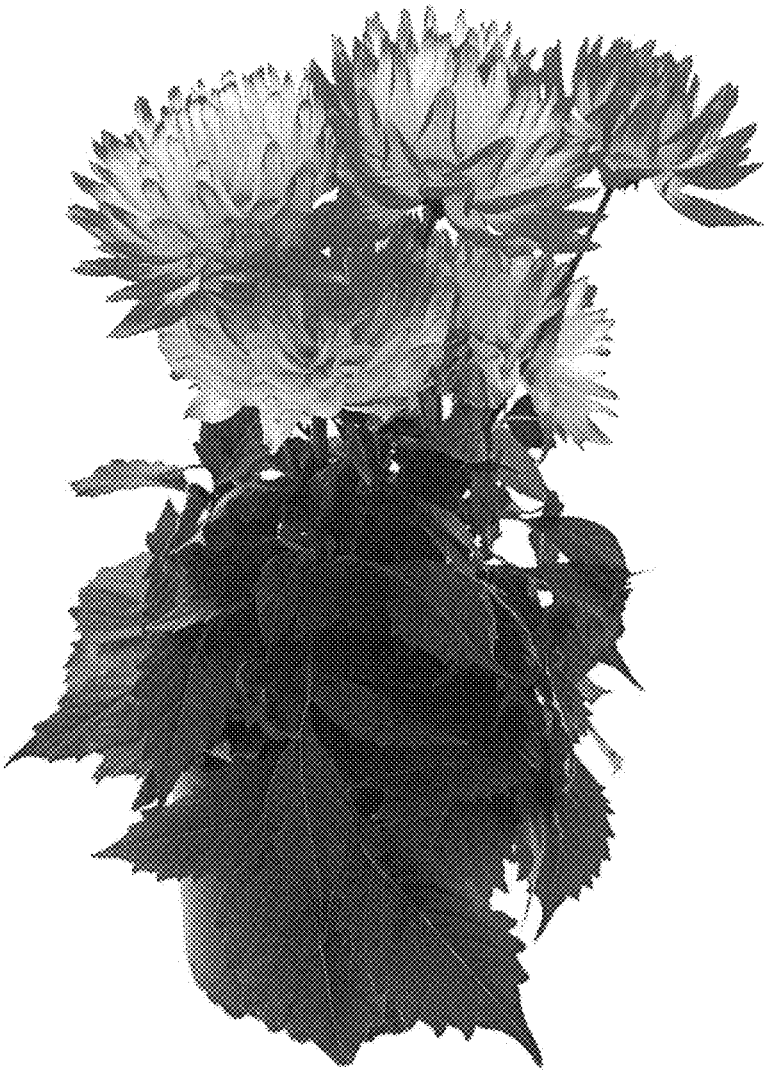

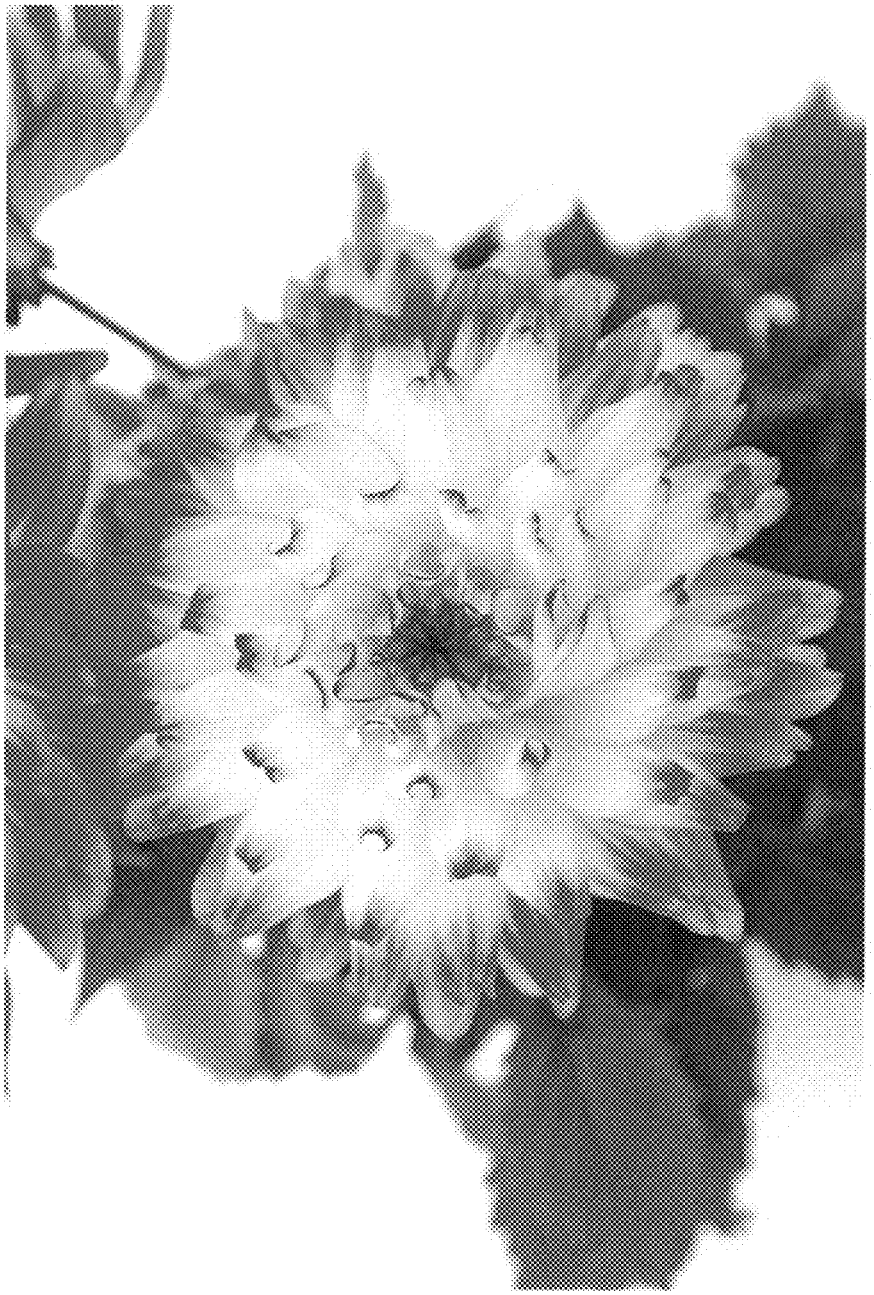

* * * * *